US012605389B2

(12) United States Patent
Pickering et al.

(10) Patent No.: US 12,605,389 B2
(45) Date of Patent: Apr. 21, 2026

(54) PI3K-δ INHIBITOR FOR USE IN TREATMENT REGIMENS

(71) Applicant: iOnctura SA, Geneva (CH)

(72) Inventors: Catherine Pickering, Geneva (CH); Lars Van Der Veen, Geneva (CH); Michael Lahn, Geneva (CH); Rebeca Zorrilla, Geneva (CH); Zoë Johnson, Geneva (CH)

(73) Assignee: iOnctura SA, Genève (CH)

( * ) Notice: Subject to any disclaimer, the term of this patent is extended or adjusted under 35 U.S.C. 154(b) by 448 days.

(21) Appl. No.: 18/271,196

(22) PCT Filed: Mar. 29, 2022

(86) PCT No.: PCT/EP2022/058283
§ 371 (c)(1),
(2) Date: Jul. 6, 2023

(87) PCT Pub. No.: WO2022/207646
PCT Pub. Date: Oct. 6, 2022

(65) Prior Publication Data
US 2024/0058351 A1 Feb. 22, 2024

(30) Foreign Application Priority Data
Mar. 29, 2021 (GB) ...................................... 2104416
Dec. 3, 2021 (GB) ...................................... 2117511

(51) Int. Cl.
*A61K 31/5377* (2006.01)
*A61K 9/20* (2006.01)
(Continued)

(52) U.S. Cl.
CPC ........ *A61K 31/5377* (2013.01); *A61K 9/2018* (2013.01); *A61K 9/2054* (2013.01);
(Continued)

(58) Field of Classification Search
CPC .............. A61K 31/5377; A61K 9/2018; A61K 9/2054; A61K 9/4858; A61K 9/4866; A61P 35/04
See application file for complete search history.

(56) References Cited

U.S. PATENT DOCUMENTS 10,654,846 B2 5/2020 Stockley et al.
2012/0238545 A1 9/2012 Gaillard et al.
(Continued)

FOREIGN PATENT DOCUMENTS

WO WO2011/058149 A1 * 5/2011
WO WO2014/121901 A1 * 8/2014
WO 2016124939 A1 8/2016

OTHER PUBLICATIONS

Clinical Trials.gov (NCT04328844, V1 Mar. 30, 2020) (Year: 2020).*
(Continued)

*Primary Examiner* — Brandon J Fetterolf
(74) *Attorney, Agent, or Firm* — Meunier Carlin & Curfman LLC

(57) ABSTRACT

A compound or a pharmaceutically acceptable salt thereof for use in a method of treatment of a disease or condition in which signalling through the PI3Kδ pathway is pathologically implicated in patients, for example cancer and inflammatory or autoimmune diseases. The compound is provided at a specified dose and has been found to have a favourable safety profile in humans, in particular with regard to hepatotoxicity, diarrhoea/colitis, respiratory infections, and hematologic toxicities.

14 Claims, 4 Drawing Sheets

(51) Int. Cl.
*A61K 9/48* (2006.01)
*A61P 35/04* (2006.01)
(52) U.S. Cl.
CPC .......... *A61K 9/4858* (2013.01); *A61K 9/4866* (2013.01); *A61P 35/04* (2018.01)

(56) References Cited

U.S. PATENT DOCUMENTS

2016/0128311 A1 5/2016 Wilkie et al.
2020/0088732 A1 3/2020 Tomasini

OTHER PUBLICATIONS

Papakonstanti et al. (MAP 2019 Poster, Nov. 2019, 1 page) (Year: 2019).*
Lim et al. (Cancer 2017; 123: 2118-2129) (Year: 2019).*
Ali, K. et al. (2008). Isoform-Specific Functions of Phosphoinositide 3-Kinases: p110δ but Not p110γ Promotes Optimal Allergic Responses In Vivo. J Immunol 180, 2538-2544.
Brock, C. et al. (2003). Roles of Gβγ in membrane recruitment and activation of p110γ/p101 phosphoinositide 3-kinase γ. J Cell Biology 160, 89-99.
Buchanan, C. M. et al. (2019). For Better or Worse: The Potential for Dose Limiting the On-Target Toxicity of PI 3-Kinase Inhibitors. Biomol 9, 402.
Committee for Medicinal Products for Human Use (CHMP) (2014). Assessment report on Zydelig. Procedure No. EMEA/H/C/003843/0000. 132 pages.
Curigliano & Shah (2019). Safety and Tolerability of Phosphatidylinositol-3-Kinase (PI3K) Inhibitors in Oncology. Drug Saf. 42 (2), 247-262.
Esposito, A. et al. (2019). Safety, Tolerability, and Management of Toxic Effects of Phosphatidylinositol 3-Kinase Inhibitor Treatment in Patients with Cancer. Jama Oncol 5, 1347-1354.
Haselmayer, P, Characterization of novel PI3Kδ inhibitors as potential therapeutics for SLE and lupus nephritis in pre-clinical studies, Frontiers in Immunology, May 2014, vol. 5, Article 233.
Horak, F. et al. (2016). Randomized phase 1 study of the phosphatidylinositol 3-kinase δ inhibitor idelalisib in patients with allergic rhinitis. J Allergy Clin Immun 137, 1733-1741.
International Searching Authority (ISA/EP). International Search Report and Written Opinion. PCT Application No. PCT/EP2022/058283. Issued on Jul. 20, 2022. 12 pages.
International Preliminary Examining Authority (IPEA/EP). International Preliminary Report on Patentability. PCT Application No. PCT/EP2022/058283. Issued on May 23, 2023. 20 pages.
Jiminez, C. et al. (2002). The p85 regulatory subunit controls sequential activation of phosphoinositide 3-kinase by Tyr kinases and Ras. J Biol Chem 277, 41556-62.
Johnson, Z. et al. (2019) Preclinical development of a novel, highly selective PI3Kδ inhibitor, IOA-244, for the treatment of solid malignancies. Annals of Oncology 30: vii27. 1 page.
Kamileri, E. et al., The Modulatory Effects of a PI3Kδ Specific Small Molecule Inhibitor (IOA-244) on Basophil Degranulation Measured by Flow Cytometry, Poster presentation at ICCS 2020 (Jul. 27-31, 2020). 1 page.
Lannutti, B. J. et al. (2011). CAL-101, a p110δ selective phosphatidylinositol-3-kinase inhibitor for the treatment of B-cell malignancies, inhibits PI3K signaling and cellular viability. Blood 117, 591-594.
Macqueen, A. et al. A novel, highly selective PI3Kδ inhibitor for the treatment of solid malignancies that express high levels of target protein as assessed by immunohistochemistry, AACR 2020, Virtual Annual Meeting II, Jun. 22-24, 2022, poster 666. 1 page.
Macqueen, A. et al. Abstract 666: A novel, highly selective treatment of solid malignancies that express high levels of target protein as assessed by immunohistochemistry. Cancer Research, vol. 80, No. 16_Supplement, Aug. 15, 2020. 1 page.
NIH National Library of Medicine. ClinicalTrials.gov Identifier: NCT04328844. A Study to Assess a PI3Kδ Inhibitor (IOA-244) in Patients With Metastatic Cancers. Version 1, Mar. 30, 2020. Post updated May 20, 2022. Downloaded on May 3, 2023 from https://beta.clinicaltrials.gov/study/NCT04328844?tab=history&a=1. 11 pages.
Papakonstanti, E. Preclinical development of a novel, highly selective PI3Kδ inhibitor, IOA-244 for the treatment of solid malignancies, MAP 2019 Poster, Nov. 2019. 1 page.
Phillips, T. J. et al. (2020). Can Next-Generation PI3K Inhibitors Unlock the Full Potential of the Class in Patients With B-Cell Lymphoma? Clin Lymphoma Myeloma Leukemia 21, 8-20.e3. 16 pages.
Vanhaesebroeck, B. et al. (2005). Signalling by PI3K isoforms: insights from gene-targeted mice. Trends Biochem Sci 30, 194-204.
Conway, J. et al. Combating pancreatic cancer with PI3K pathway inhibitors in the era of personalised medicine. Gut, 2019; 68:742-758.
Borazanci E., et al., "A Phase Ib Study of Single Agent Idelalisib Followed by Idelalisib in Combination with Chemotherapy in Patients with Metastatic Pancreatic Ductal Adenocarcinoma," Oncology, 2020.
Burris III H.A., et al., "Improvements in Survival and Clinical Benefit with Gemcitabine as First-line Therapy for Patients with Advanced Pancreas Cancer: A Randomized Trial," Journal of Clinical Oncology, United States, Jun. 1997, vol. 15, No. 6, pp. 2403-2413.
International Search Report and Written Opinion for International Application No. PCT/EP2022/058296, dated Jul. 25, 2022, 24 Pages.
Ali et al. "Inactivation of the PI3K p110δ breaks regulatory T cell-mediated immune tolerance to cancer", Nature, 510 (7505): 407-411 (Jun. 19, 2014).
Mosele F., et al., "92P Detection of PIK3CA Mutation by Circulating DNA During Chemotherapy: A Tool to Identify Hard-to-Treat Metastatic Breast Cancers," DOI: https://doi.org/10.1093/annonc/mdz413.096.
Zhang et al. "Regulatory T-cell Depletion Alters the Tumor Microenvironment and Accelerates Pancreatic Carcinogenesis", Cancer Discovery, 422-439 (Mar. 2020).

* cited by examiner

PI3K-δ INHIBITOR FOR USE IN TREATMENT REGIMENS

This application is a national stage application filed under 35 U.S.C. § 371 of PCT/EP2022/058283 filed Mar. 29, 2022, which claims priority from GB2104416.9 filed 29 Mar. 2021 and from GB 2117511.2 filed 3 Dec. 2021, the contents and elements of which are herein incorporated by reference for all purposes.

FIELD OF THE INVENTION

The present invention relates to treatment of a disease or condition in which signalling through the PI3Kδ pathway is pathologically implicated with a PI3Kδ inhibitor. Such diseases or conditions include cancer and multiple inflammatory and autoimmune diseases.

BACKGROUND

PI3Ks belong to a family of lipid signalling kinases that phosphorylate phosphoinositides at the D3 position of the inositol ring. PI3Ks are divided into 3 classes (Class I, II, and III) according to their structure, regulation and substrate specificity. Class I PI3Ks, which include PI3Kα, PI3Kβ, PI3Kγ, and PI3Kδ are lipid kinases that catalyse the phosphorylation of phosphatidylinositol-4,5-bisphosphate, giving rise to phosphatidylinositol-3,4,5-trisphosphate (PIP3). PIP3 functions as a second messenger that controls a number of cellular processes, including growth, survival, adhesion, and migration.

All 4 class I PI3K isoforms exist as heterodimers, composed of a catalytic subunit (p110) and a tightly associated regulatory subunit that controls expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, Hernandez et al. 2002); PI3Kγ associates with 2 regulatory subunits (p101 and p84) and its activation is driven by the activation of G-protein-coupled receptors (Brock, Schaefer et al. 2003). PI3Kα and PI3Kβ are ubiquitously expressed. In contrast, PI3Kγ and PO3Kδ are predominantly expressed in leukocytes (Vanhaesebroeck, Ali et al. 2005).

The PI3K pathway is frequently activated in a variety of solid tumours and haematological malignancies, making PI3K an attractive therapeutic target in oncology. This has led to a considerable interest in the field for developing inhibitors targeting this pathway (Buchanan 2019). Although many PI3K inhibitors have reached different stages of clinical development, very few PI3K inhibitors have been approved for clinical use. While these agents are effective clinically, their use is associated with a number of serious class-related as well as drug-specific adverse effects. Some of these are thought to be immune-mediated and include cutaneous reactions, severe diarrhoea with or without colitis, hepatotoxicity and pneumonitis. PI3K inhibitors also induce various metabolic abnormalities such as hyperglycaemia and hypertriglyceridaemia.

As a result, many new PI3K inhibitors with varying degrees of target selectivity have been synthesised in hope of improved safety and efficacy. Some of these are currently under clinical investigations for use in a variety of solid tumours, as well as haematological malignancies. However, evidence from early clinical trials suggests that these newer agents are also associated not only with class-related side-effects, but also other serious and unexpected adverse effects. Consequently, the development of many of these new agents has been discontinued.

As a class, PI3Kδ inhibitors are associated with serious dermatological, myelosuppressive, metabolic, gastrointestinal and respiratory adverse effects (Curigliano 2019). Unlike p110α and p110β, which are ubiquitously expressed, p110δ is mainly expressed in leukocytes (such as T and B cells) and therefore PI3Kδ inhibitors have been used to target relapsed or refractory lymphoma including, but not limited to, CLL, mantle cell lymphoma and non-Hodgkin lymphoma (Buchanan 2019). Unsurprisingly, these PI3Kδ isoform-specific inhibitors are also noted for hematologic toxicities including anaemia, thrombocytopenia, leucocytosis, haemolysis and neutropenia. Inhibition of PI3Kδ leads to activation of the immune response, which is believed to also account for some of the adverse reactions to these agents, for example the PI3Kδ selective idelalisib. Idelalisib-induced colitis, hepatitis and pneumonitis are believed to be immune-mediated effects and higher incidences of idelalisib-induced diarrhoea, pneumonitis and raised hepatic transaminases are observed in immunocompetent patients. The FDA-approved label of idelalisib includes a detailed black box warning concerning its potential for "Fatal and Serious toxicities: Hepatic, severe diarrhoea, colitis, pneumonitis, infections and intestinal perforations". Therefore, the safety of currently approved PI3K inhibitors, especially when given for a prolonged time, has been under intense scrutiny.

Adverse events (AEs) experienced by patients treated with PI3Kδ inhibitors are clinically significant, potentially limiting their use (Phillips 2020). Currently, it is unknown whether dose interruptions/modifications due to adverse effects have a negative impact on the efficacy of the PI3Kδ inhibitors. Generally believed target or class-specific toxicities associated with PI3Kδ inhibitors are hepatotoxicity, diarrhoea/colitis, respiratory infections, and haematological toxicities.

Haematological toxicities such as neutropenias are often noted in trial outcomes as common laboratory abnormalities. Hepatoxicities are most often assessed by liver transaminase elevations in blood and graded in relation to their severity (grade 1 being minimal while grade 5 is often lethal). Grade 3 alanine aminotransferase (ALT) and aspartate aminotransferase (AST) levels commonly observed with PI3Kδ inhibitors often lead to dose interruption or modification and, less frequent, to treatment discontinuation. Diarrhoea or colitis is reported in up to one third of patients treated with PI3Kδ inhibitors and typically require treatment with anti-diarrhetic- or anti-inflammatory drugs. Respiratory infections are observed in up to 20% of patients receiving idelalisib and typically patients on PI3Kδ inhibitors are given anti-infective prophylaxis.

In view of the above, there is a need in the art for PI3K modulators that inhibit specific PI3K isoforms, in particular PI3Kδ, with high selectivity over other isoforms and that at the same time have favourable safety profiles (in particular with regard to elevated liver enzymes, diarrhoea and neutropenia). Moreover, there is a need in the art for improved ways of treating (and preventing) diseases with PI3Kδ pathway involvement by compounds with high selectivity and favourable safety profiles (in particular with regard to elevated liver enzymes, diarrhoea and neutropenia).

The present inventors, recognising this need, set about devising the present invention. Amongst the myriad disclosures relating to PI3K inhibitor compounds, WO2011058149 describes Tricyclic Pyrazol Amine Derivatives which are PI3K inhibitors and their use for treating autoimmune diseases, inflammatory disorders, multiple sclerosis and other diseases like cancers.

SUMMARY OF THE INVENTION

In a first aspect, the invention provides a compound of Formula I

Formula I

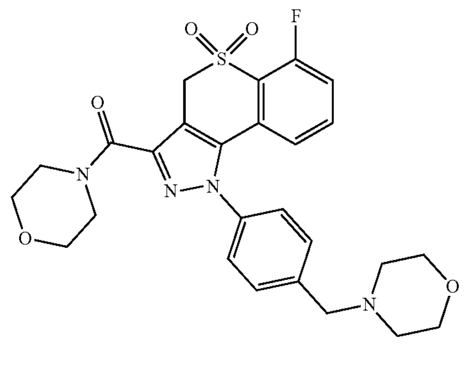

or a pharmaceutically acceptable salt thereof,
for use in a method of treatment of a disease or condition in which signalling through the PI3Kδ pathway is pathologically implicated in patients (such as but not limited to an imbalance of the immune cell responses or expression in tumour cells), the method comprising administration of the compound of Formula I in dose of between 18 mg and 108 mg of the compound per day. In some embodiments, the dose is between 18 mg and 72 mg per day. Preferably, the dose is about 36 mg per day. In another embodiment, preferably the dose is about 72 mg per day.

As described and exemplified herein, the pharmaceutically acceptable salt is preferably the hemifumarate. That is, the compound is provided as a salt of Formula Ia.

Formula Ia

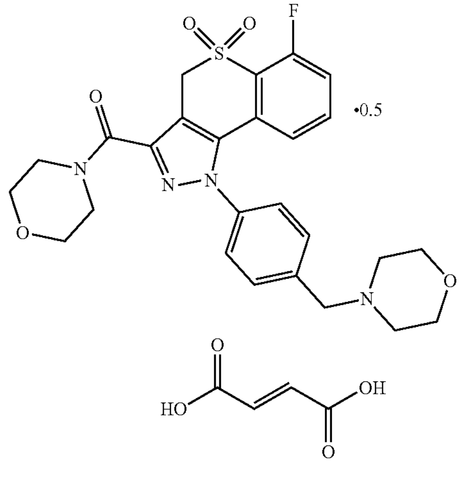

Accordingly, the invention provides a salt of Formula Ia for use in a method of treatment of a disease or condition in which signalling through the PI3Kδ pathway is pathologically implicated in patients (such as but not limited to an imbalance of the immune cell responses or expression in tumour cells), the method comprising administration of the salt of Formula Ia in a dose of between 20 mg and 120 mg of the salt per day. In some embodiments, the dose is between 20 mg and 80 mg of the salt per day. Preferably, the dose is about 40 mg per day. In another embodiment, preferably the dose is about 80 mg per day.

The dose may be administered in a once daily regimen. That is, the daily dose may be taken in one or more dosage units in a single sitting. Accordingly, in some embodiments the administration is once daily. This may be referred to as QD (quaque die).

Suitably, the administration is oral. This may be referred to as P.O. (per os).

In other words, in some embodiments the dose of the salt of Formula Ia may be 20-120 mg, more preferably 20-80 mg, more preferably 30-60 mg, more preferably 30-50 mg, most preferably about 40 mg, P.O. QD. In other embodiments the dose of the salt of Formula Ia may be 20-120 mg, more preferably 20-80 mg, more preferably 30-100 mg, more preferably 30-80 mg, more preferably 40-80 mg, most preferably about 80 mg, P.O. QD.

Suitably, more than one solid dosage unit per administration is used. In other words, the dose is divided into multiple dosage units. For example, the administration may comprise two solid dosage units, each dosage unit comprising 20 mg of a salt of Formula Ia. In another example the administration may comprise four solid dosage units, each dosage unit comprising 20 mg of a salt of Formula Ia.

Accordingly, in a further aspect the invention may provide a solid dosage unit comprising 20 mg of a salt of Formula Ia.

Accordingly, in a further aspect the invention may provide a solid dosage unit comprising 5 mg of a salt of Formula Ia.

In another embodiment one solid dosage unit per administration is used. For example, the administration may comprise one solid dosage unit comprising 40 mg of a salt of formula Ia. In another embodiment the administration may comprise one solid dosage unit comprising 80 mg of a salt of formula Ia.

Accordingly, in a further aspect the invention may provide a solid dosage unit comprising 80 mg of a salt of Formula Ia.

Accordingly, in a further aspect the invention may provide a solid dosage unit comprising 40 mg of a salt of Formula Ia.

In some embodiments, the salt of Formula Ia is formulated in a pharmaceutical composition comprising microcrystalline cellulose, mannitol, croscarmellose sodium and magnesium stearate. In some embodiments the pharmaceutical composition is provided in shell capsule.

The methods of the present invention are directed to the treatment of a disease or condition in which signalling through the PI3Kδ pathway is pathologically implicated (such as but not limited to an imbalance of the immune cell responses or expression in tumour cells). Such diseases or conditions include inflammatory diseases, autoimmune diseases and cancer. In other words, the method may be a method of treating a disease or condition selected from inflammatory diseases, autoimmune diseases and cancer.

In some embodiments the method is a method of treatment of cancer.

In some embodiments, the cancer is selected from skin cancer, eye cancer, endometrial cancer, ovarian cancer, bladder cancer, gastric cancer, lung cancer, breast cancer, pancreatic cancer, myelofibrosis, leukaemia, lymphoma, multiple myeloma (including Morbus Waldenström), brain cancer, mesothelioma, head and neck cancer, prostate cancer, liver cancer, kidney cancer and colorectal cancer. For example, the cancer may be melanoma, lymphoma, myelofibrosis, non-small cell lung cancer or mesothelioma. In some cases, melanoma is advanced or metastatic melanoma or ocular/uveal melanoma. Advanced or metastatic melanoma may be histologically confirmed, unresectable Stage III or IV melanoma. In some cases, the cancer is B cell lymphoma. In some cases, the cancer is T cell lymphoma. In some cases, the cancer is melanoma. In some cases, the cancer is uveal melanoma.

In some embodiments, the inflammatory or autoimmune disease may be activated PI3Kδ syndrome (APDS), allergic diseases, asthma, chronic obstructive pulmonary disease (COPD), inflammatory bowel disease, Crohn's disease, psoriasis, rheumatoid arthritis (RA), multiple sclerosis (MS), primary Sjögren's syndrome, pemphigus vulgaris, autoimmune haemolytic anaemia, systemic lupus erythematosus (SLE), lupus nephritis, membranous nephropathy, glomerulonephritis, diabetic nephropathy, vasculitis, and idiopathic thrombocytopenia purpura (ITP).

In some preferred embodiments, the treatment does not result in any clinically significant treatment-related alanine aminotransferase (ALT) or aspartate aminotransferase (AST) elevation in patients. In some preferred embodiments, the treatment does not result in treatment-related grade 3 diarrhoea or colitis.

In some preferred embodiments, the treatment does not result in any clinically significant treatment-related neutropenia in patients.

In some preferred embodiments, the treatment results in longer time on treatment in the absence of serious adverse effects.

The present invention further provides solid dosage forms for use in these methods. Suitable solid dosage forms include tablets and hard- or soft-shell capsules.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Figure 1A:
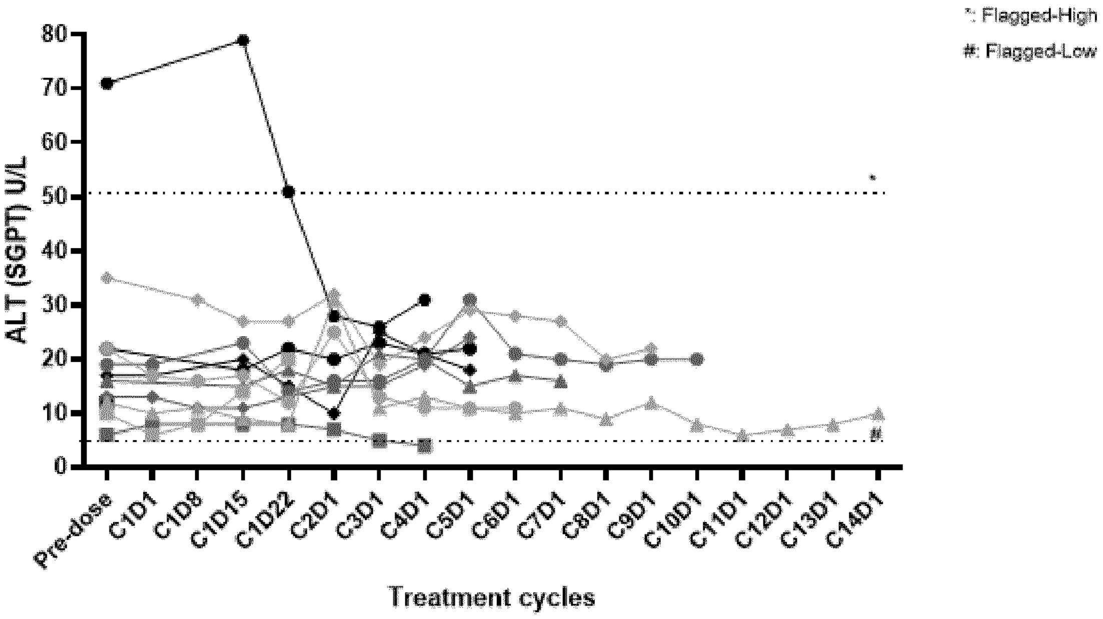
FIGS. 1*a* and 1*b* show measured ALT levels in patients treated with Compound 1.

Aspects and embodiments of the present invention will now be discussed. Further aspects and embodiments will be apparent to those skilled in the art. All documents mentioned in this text are incorporated herein by reference.

Compound 1

Compound 1 is example 339 in WO2011058149, which document is incorporated herein by reference in its entirety. Its structure is according to Formula I:

Formula I

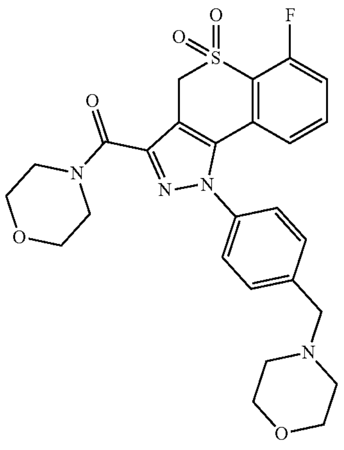

In IUPAC nomenclature, the above Compound 1 may be referred to as 6-Fluoro-3-(morpholin-4-ylcarbonyl)-1-[4-(morpholin-4-ylmethyl)phenyl]-1,4-dihydrothiochromeno [4,3- c]pyrazole 5,5-dioxide. Alternatively, the structural formula shown above may be described as [6-fluoro-1-(4-morpholin-4-yl-methylphenyl)-5,5-dioxo-4,5-dihydro-1H-5λ6-thiochromeno[4,3-C]pyrazol-3-yl]-morpholin-4-yl-methanone.

Compound 1 can be prepared and characterized as described in published patent application WO 2011058149 A1 (see compound 339 on p. 69; the preparation on p. 303-307; and the characterization on p. 481 with p. 414-418), which information is specifically incorporated herein by reference.

Based on the process disclosed in WO 2011/058149 A1, the authors of Haselmayer et al. describe a five-step preparation procedure for the compound (Haselmayer, 2014). This procedure starts with reaction of 8-fluoro-2,3-dihydro-4Hthiochromen-4-one with diethyl oxalate in the presence of sodium ethoxide. The intermediate is cyclized with 4-(4-hydrazinylbenzyl)morpholine to form a pyrazole ring. The thioether is then oxidized to the corresponding sulfone by reaction with meta-chloroperbenzoic acid, followed by saponification of the ethyl ester into the corresponding acid and subsequent coupling with morpholine to yield the compound of formula I.

Alternatively, the intermediate of the reaction of 8-fluoro-2,3-dihydro-4H-thiochromen-4-one with diethyl oxalate in the presence of sodium ethoxide is cyclized with 4-hydrazinobenzoic acid. The benzoic acid is reduced using borane-THF complex and the thioether is oxidized to the corresponding sulfone by reaction with meta-chloroperbenzoic acid. Saponification of the ethyl ester into the corresponding acid and chlorination of both the acid and alcohol with excess thionyl chloride in the presence of dimethylformamide and subsequent coupling with morpholine then yields Compound 1.

Compound 1 may be provided as a pharmaceutically acceptable salt. Suitable pharmaceutically acceptable salts are known in the art. Some pharmaceutically acceptable salts of Compound 1 are described in WO2014121901, which is incorporated by reference in its entirety.

As used herein, Compound 1 is provided as an anhydrous hemifumarate salt (formula illustrated). Its synthesis and characterisation are described in WO2014121901 (page 4). It is referred to as solid form A1. A hemifumarate hydrate (H1) has also been identified. The anhydrous hemifumarate salt used is crystalline and has a powder X-ray peak list as described in WO2014121901. It will be appreciated that the findings of the invention are not limited to use of this solid form, although it is preferred.

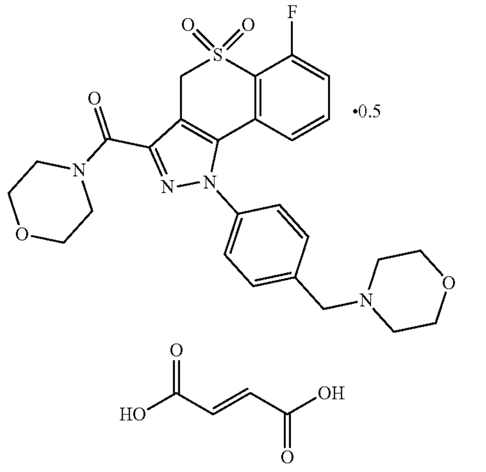

Haselmayer et al. also describe the characterisation of the compound as highly selective PI3Kδ inhibitor. The favourable in vitro and in vivo properties of Compound 1 are further described by Johnson et al. (Johnson, Z. et al., AACR 2020, poster 666).

Formulation

Compound 1 is suitably provided as a hemifumarate as described above. Suitability, Compound 1 is provided in a pharmaceutical composition formulated for oral administration. The pharmaceutical composition may be provided in a capsule or may be provided in a tablet. In some cases, it is provided in a tablet, for example, as a coated or non-coated tablet produced by compression of a powdered or granulated composition. In other cases, it is provided in a capsule, for example, as a powdered or granulated composition within a hard- or soft-shell capsule, for example, a hydroxymethyl cellulose (HPMC) capsule. In other words, an oral dosage form is preferred.

The formulation suitably comprises one or more pharmaceutically acceptable fillers, disintegrants, glidants, and/or lubricants.

In some cases, the oral dosage form may comprise 5 mg of Compound 1, provided as the hemifumarate. In some cases, the oral dosage form may comprise 20 mg of Compound 1, provided as the hemifumarate. Both oral dosage forms have been made as described in Table 1. It will be appreciated that, for the doses of the method, a comparatively low dosage burden (number of capsules or tablets) is placed on patients, especially when 20 mg solid dosage forms are used. This is advantageous for patient compliance.

It will however be appreciated that for some patients, smaller dosage forms may be preferred, for example if a patient has difficulties swallowing. Even using the smaller 5 mg solid dosage form, the burden on patients (number of capsules or tablets) is not uncommon in treatment of the conditions claimed.

TABLE 1

| | | Quantity per capsule (mg) | |
|---|---|---|---|
| Ingredient | Function | 5 mg | 20 mg |
| Compound 1 hemifumarate | Active substance | 5.00* | 20.00* |
| Microcrystalline cellulose | Filler | 24.34 | 97.35 |
| Mannitol | Filler | 24.34 | 97.35 |
| Croscarmellose sodium | Disintegrant | 2.26 | 9.04 |
| Silica, colloidal hydrated | Glidant | 0.28 | 1.13 |
| Magnesium stearate (vegetable origin) | Lubricant | 0.28 | 1.13 |
| Hydroxypropyl methyl cellulose (HPMC) capsule, size 5 (5 × 11 mm), white | Capsule shell | 1 | NA |
| Hydroxypropyl methyl cellulose (HPMC) capsule, size 1 (6 × 19 mm), white | Capsule shell | NA | 1 |
| Total capsule fill weight | | 56.50 | 226.00 |

*Corrected for purity (according to Certificate of Analysis).

The oral dosage form may also comprise 40 mg of Compound 1, provided as the hemifumarate. The oral dosage form may also comprise 80 mg of Compound 1, provided as the hemifumarate. Both oral dosage forms can be made similarly to the dosage forms described Table 1. It will be appreciated that, for the doses of the method, the lowest dosage burden (number of capsules or tablets) is placed on patients, when a single solid dosage form is used. This is most advantageous for patient compliance.

Accordingly, the invention further relates to a pharmaceutical composition comprising Compound 1, preferably provided as the hemifumarate salt, formulated for oral administration.

An exemplary formulation includes Compound 1 hemifumarate, microcrystalline cellulose, mannitol, croscarmellose sodium and magnesium stearate. The formulation may be provided in a solid dosage form, for example as tablet or powder or granulated composition encapsulated in a shell capsule. It will be appreciated that a single tablet can accommodate a higher dose of Compound 1 hemifumarate than a single capsule. Therefore, tablets are preferred for higher dose units. Tablets may be coated to improve taste or swallowing.

The amount of Compound 1 hemifumarate may be 5 mg to 20 mg, for example 5 mg or 20 mg. In another embodiment the amount of compound 1 may be 5 mg to 80 mg, for example 5 mg, 20 mg, 40 mg or 80 mg.

Accordingly, in some embodiments the invention provides a solid dosage unit comprising a pharmaceutical composition comprising 5 mg of Compound 1 hemifumarate. Accordingly, in some embodiments the invention provides a solid dosage unit comprising a pharmaceutical composition comprising 20 mg of Compound 1 hemifumarate. Accordingly, in some embodiments the invention provides a solid dosage unit comprising a pharmaceutical composition comprising 40 mg of Compound 1 hemifumarate. Accordingly, in some embodiments the invention provides a solid dosage unit comprising a pharmaceutical composition comprising 80 mg of Compound 1 hemifumarate.

Accordingly, in some embodiments the invention provides a tablet comprising a pharmaceutical composition comprising 40 mg of Compound 1 hemifumarate. Accordingly, in some embodiments the invention provides a tablet comprising a pharmaceutical composition comprising 80 mg of Compound 1 hemifumarate. It will be appreciated that the pharmaceutical composition of the tablet can be similar to that of the capsule or can be optimised for tableting.

Methods of the Invention

As described in more detail below, the present inventors have surprisingly found that Compound 1 has a favourable safety profile in humans, in particular with regard to hepatotoxicity, diarrhoea/colitis, respiratory infections, and hematologic toxicities. Moreover, treatment of patients with Compound 1 does not lead to elevated liver enzymes, diarrhoea and neutropenia. Thus, a PI3K inhibitor with specificity for the isoform δ and favourable safety characteristics in patients can be provided.

Further advantageous properties of methods of treatment using Compound 1 may include one or more of higher efficacy, longer treatment duration, less dose reductions or interruptions or discontinuations.

In other words the inventors have found that, surprisingly, patients (in this case patients with melanoma, uveal melanoma and mesothelioma; hence, this is anticipated to be applicable to all human subjects) can be treated with Compound 1 with fewer adverse effects than would be expected for treatment regimens using a PI3K inhibitor. This may make treatment suitable for long term prescription without dose reduction or interruption.

In the clinical trial and examples described herein, Compound 1 is administered as the hemifumarate salt. Accordingly, in some cases Compound 1 is administered as the hemifumarate salt. However, it will be understood that the invention is not so limited, and other solid forms (for example, other pharmaceutically acceptable salts) are envisaged.

The weight equivalent of Compound 1 as a free base in a 40 mg dose is calculated at about 36 mg (that is, about 90% of the weight of Compound 1 hemifumarate corresponds to the free base, with the remaining about 10% of the weight corresponding to the salt former acid.

The weight equivalent of Compound 1 as a free base in a 80 mg dose is calculated at about 72 mg (that is, about 90% of the weight of Compound 1 hemifumarate corresponds to the free base, with the remaining about 10% of the weight corresponding to the salt former acid.

The invention therefore relates to a method of treatment of a disease or condition in which signalling through the PI3Kδ pathway is pathologically implicated in patients, the method comprising administration of Compound 1 in an amount of between 18 mg and 108 mg per day. In some cases, the amount is between 18 mg and 72 mg per day. In some cases, the amount is between 27 and 54 mg per day. In some cases, the amount is between 27 and 45 mg per day, for example about 36 mg per day. In some cases, the amount is between 27 and 108 mg per day. In some cases, the amount is between 27 and 72 mg per day. In some cases, the amount is between 36 and 90 mg per day, for example about 72 mg per day. In some cases, the amount is between 36 and 72 mg per day.

Where Compound 1 is administered as the hemifumarate salt (Formula Ia), the invention relates to a method of treatment of a disease or condition in which signalling through the PI3Kδ pathway is pathologically implicated in patients, the method comprising administration of Compound 1 as the hemifumarate in an amount of between 20 mg and 120 mg per day. In some cases, the amount is between 20 mg and 80 mg per day. In some cases, the amount is between 30 and 60 mg per day. In some cases, the amount is between 30 and 50 mg per day, for example about 40 mg per day. In some cases, the amount is between 30 and 120 mg per day. In some cases, the amount is between 30 and 80 mg per day. In some cases, the amount is between 40 and 100 mg per day, for example about 80 mg per day. In some cases, the amount is between 40 and 80 mg per day.

Lower doses have also been investigated and are envisaged. Accordingly, it will be appreciated that in any method described herein the method may comprise administration of Compound 1 in an amount of between 9 mg and 108 mg per day. In some cases, the amount of compound 1 is between 9 mg and 72 mg per day. Where Compound 1 is administered as the hemifumarate salt, in any method described herein the method may comprise administration of Compound 1 as the hemifumarate salt in an amount of between 10 mg and 120 mg per day. In some cases, the amount of compound 1 as the hemifumarate salt is between 10 mg and 80 mg per day.

Inhibition of the PI3Kδ pathway in patients can be demonstrated by measuring the pharmacodynamic activity (PD) of Compound 1 in blood samples. A specific PD marker for PI3Kδ inhibition in blood is CD63 expression on basophils. Treatment of patients with Compound 1 as the hemifumarate salt results in a dose dependent reduction of the percentage CD63 positive basophils in blood samples of patients comparable to that reported for other PI3Kδ inhibitors (for example idelalisib). Especially at the dose of 40 mg the percentage of CD63 positive basophils is low in all samples measured confirming effective inhibition of the PI3Kδ pathway during the course of treatment. Especially at the dose of 80 mg the percentage of CD63 positive basophils is also low in all samples measured confirming effective inhibition of the PI3Kδ pathway during the course of treatment.

Accordingly, certain preferred embodiments relate to a dose of 40 mg of a salt of Formula Ia, or a dose of 36 mg of a compound of Formula I.

However, it will be appreciated that higher doses are encompassed and envisaged. For example, the dose may be 60 mg of a salt of Formula Ia, or a dose of 54 mg of a compound of Formula I. For example, the dose may be 80 mg of a salt of Formula Ia, or a dose of 72 mg of a compound of Formula I, which may be preferred in some embodiments.

In some cases, lower doses are envisaged. For example the dose may be 10 mg of a salt of Formula Ia, or a dose of 9 mg of a compound of Formula I.

The inventors have found a once daily dose effective and well-tolerated. Once daily dosing offers advantages when compared to some known and used PI3K inhibitors (for example, idelasib is prescribed as a twice daily 150 mg dose unless dosage reduction due to adverse effects is required). A once daily dose improves patient experience and may improve patient compliance. Patients with, especially advanced, cancers often experience a considerable pill burden and may have difficulty swallowing. Accordingly, in the methods of the invention the dose may be taken once daily. In other words, the dose is not divided and spaced throughout the day. It may be taken as in a single dosage unit (for example, a single tablet or capsule), or in multiple dosage forms (for example, as two or more tablets or capsules).

Accordingly, in some cases the method comprises administering one or more solid dosage units. For example, in some cases the daily dose is 40 mg and the method comprises administering two 20 mg solid dosage units (that is, a solid dosage unit comprising 20 mg of Compound 1 as the hemifumarate) or, more preferably, one 40 mg solid dosage unit.

In another example, the daily dose may be 60 mg and administration may comprise three solid dosage units, each dosage unit comprising 20 mg of a salt of Formula Ia. In another example, the daily dose may be 80 mg and the administration may comprise four solid dosage units, each dosage unit comprising 20 mg of a salt of Formula Ia. In another embodiment the administration may comprise two dosage units comprising 40 mg of a salt of Formula Ia or, more preferably, one dosage units comprising 80 mg of a salt of Formula Ia.

As described herein, the inventors have identified that Compound 1 has a surprisingly good safety profile in humans, observing that treatment may result in less treatment-related grade 3 alanine aminotransferase (ALT) or aspartate aminotransferase (AST) elevation than would be expected for an inhibitor of this class.

Accordingly, in some cases treatment of patients with Compound 1 does not result in treatment-related grade 3 alanine aminotransferase (ALT) or aspartate aminotransferase (AST) elevation in more than 5% of patients. More preferably treatment of patients with Compound 1 does not result in treatment-related grade 3 alanine aminotransferase (ALT) or aspartate aminotransferase (AST) elevation in more than 1% of patients. Most preferably, treatment of patients with Compound 1 does not result in any clinically significant treatment-related alanine aminotransferase (ALT) or aspartate aminotransferase (AST) elevation in patients.

The inventors have further identified from initial trials that treatment with Compound 1 results in fewer adverse effects than is expected for inhibitors of this class. In particular, less common occurrence of serious diarrhoea and/or colitis is expected. This is most surprising especially for the 80 mg dose as at this dose level almost complete inhibition of PI3Kδ activity can be expected.

Accordingly, in some cases treatment of patients with Compound 1 does not result in treatment-related grade 3 diarrhoea or colitis in more than 5% of patients. More preferably treatment of patients with Compound 1 does not result in treatment-related grade 3 diarrhoea or colitis in more than 1% of patients. Most preferably, treatment of patients with Compound 1 does not result in any clinically significant treatment-related diarrhoea or colitis in patients.

As described in the examples, the inventors have observed that treatment with Compound 1 does not appear to result in clinically significant treatment-related decrease in neutrophils below the normal range.

Accordingly, in some cases treatment of patients with Compound 1 does not result in treatment-related grade 3 neutropenia in more than 5% of patients. More preferably treatment of patients with Compound 1 does not result in treatment-related grade 3 neutropenia in more than 1% of patients. Most preferably, treatment of patients with Compound 1 does not result in any clinically significant treatment-related neutropenia in patients.

It will be appreciated that adverse effects may interrupt or even preclude ongoing treatment, depending on their severity. Where serious adverse effects are noted, treatment may be paused, dosage adjusted downwards (with potentially deleterious influence on efficacy) or even lead to a decision to terminate treatment. In the treatment of cancer, any of these interruptions may have significant negative effects on patient health, prognosis, and/or morale.

The inventors have identified from initial trials that treatment with Compound 1 results in longer time on treatment than is expected for inhibitors of this class. In particular, longer time on treatment in absence of serious adverse effects is expected to benefit patients. In solid tumours this has already resulted in a partial anti-tumour response in one patient at the 20 mg dose and in to prolonged stable disease in several other patients at the 40 mg and 80 mg dose levels.

Its excellent safety profile means that Compound 1 offers treatment regimens that may be suitable for long term use without interruption. Accordingly, it is envisaged that patients may be prescribed a treatment regimen for a duration of months. In some cases, the treatment is prescribed for at least 1 month. In some cases, the treatment is prescribed for at least 2 months. In some cases, the treatment is prescribed for at least 3 months. In some cases, the treatment is prescribed for at least 4 months. In some cases, the treatment is prescribed for at least 5 months. In some cases, the treatment is prescribed for at least 6 months. In some cases, the treatment is prescribed for at least 1 year.

In some cases, the treatment duration is at least 1 month without interruption. In some cases, the treatment duration is at least 2 months without interruption. In some cases, the treatment duration is at least 3 months without interruption. In some cases, the treatment duration is at least 4 months without interruption. In some cases, the treatment duration is at least 5 months without interruption. In some cases, the treatment duration is at least 6 months without interruption. In some cases, the treatment duration is at least 1 year without interruption.

In some cases, the treatment is administered in 28 day cycles. The treatment duration can be multiple 28 day cycles without interruption. In some cases, the treatment duration is at least 1 year in 28 day cycles without interruption.

It will be appreciated that the methods of the invention may be particularly useful in the treatment of certain patient groups, for example elderly and/or frail patients who are not presently eligible to receive PI3Kδ inhibitors because of their poor tolerability.

Accordingly, in some cases the patient is 50 years old or older, for example 55 years old or older, for example 60 years old or older, for example 65 years old or older, for example 70 years old or older, for example 75 years old or older, for example 80 years old or older.

In some cases, the patient is or would be considered by a physician unsuitable for treatment with idelalisib and/or other PI3Kδ inhibitors.

In some cases, the patient is a patient who has been previously diagnosed as suffering from a gastrointestinal disorder, for example colitis or chronic diarrhoea.

Treatment of a Disease or Condition in which Signalling Through the PI3Kδ Pathway is Pathologically Implicated Using Compound 1

Compound 1 is a PI3Kδ inhibitor. It is recognised in the art that the PI3K pathway is frequently activated in a variety of diseases. Accordingly, the methods of the present invention are directed to the treatment of diseases, that involve, preferably are causally linked to, activation of the PI3K pathway (compared to the state in a healthy individual), such as for example an inflammatory disease, autoimmune disease or cancer.

The methods of the present invention may therefore relate to treatment of a disease or disorder characterised by upregulation of the PI3K pathway. The methods of the present invention may therefore relate to treatment of a disease or disorder by modulation of PI3K pathway in a patient.

In some embodiments, the inflammatory or autoimmune disease may be activated PI3Kδ syndrome (APDS), allergic diseases, asthma, chronic obstructive pulmonary disease (COPD), inflammatory bowel disease, Crohn's disease, psoriasis, rheumatoid arthritis (RA), multiple sclerosis (MS), primary Sjögren's syndrome, pemphigus vulgaris, autoimmune haemolytic anaemia, systemic lupus erythematosus (SLE), lupus nephritis, membranous nephropathy, glomerulonephritis, diabetic nephropathy, vasculitis, and idiopathic thrombocytopenia purpura (ITP).

The PI3K pathway is frequently activated in solid tumours and haematological malignancies. In some embodiments the methods of the present invention are directed towards the treatment of cancer. The cancer may be a solid tumour or a haematological malignancy. In some embodiments the cancer is selected from skin cancer, eye cancer, endometrial cancer, ovarian cancer, bladder cancer, gastric cancer, lung cancer, breast cancer, pancreatic cancer, myelofibrosis, leukaemia, lymphoma, multiple myeloma (including Morbus Waldenström), brain cancer, mesothelioma, head and neck cancer, prostate cancer, liver cancer, kidney cancer and colorectal cancer.

In some embodiments, the cancer is melanoma, lymphoma, myelofibrosis, non-small cell lung cancer or mesothelioma.

In some embodiments, the melanoma is selected from advanced or metastatic melanoma or ocular/uveal melanoma. Advanced or metastatic melanoma may be histologically confirmed, unresectable Stage III or IV melanoma. In some embodiments the melanoma is uveal melanoma.

In some embodiments, the lymphoma is selected from B cell lymphoma or T cell lymphoma.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

EXAMPLES

Example 1

First-In-Human Dose Study of IOA-244 in Patients with Advanced or Metastatic Cancers In order to determine the safety and tolerability profile of Compound 1 in patients a clinical study in patients with advanced or metastatic cancers was performed. The clinical study is described on clinicaltrials.gov under number NCT04328844, and Compound 1 is provided as the hemifumarate salt. The estimated primary completion date is September 2022, and the estimated study completion date is April 2023.

Example 2

Measurement of ALT Levels in Blood Samples of Patients Treated with Compound 1

Figure 1B:
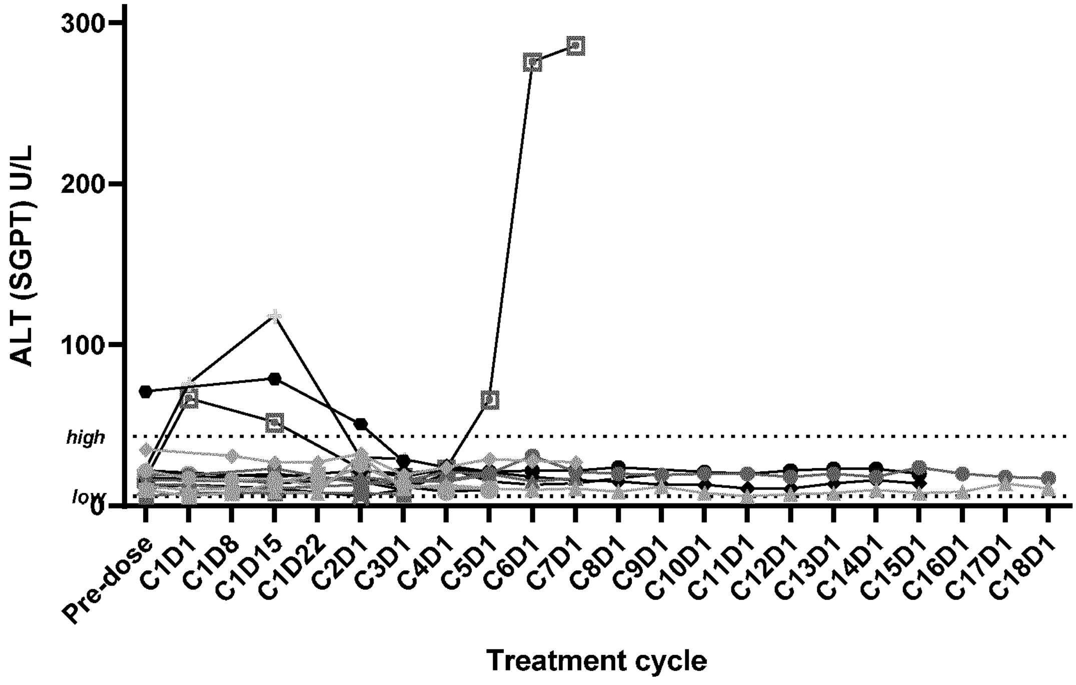

The hepatotoxicity of Compound 1 in patients was determined by measuring the levels ALT in blood samples of patients treated with Compound 1 hemifumarate. The initial dose groups were 10, 20 and 40 mg once daily, taken as an oral formulation as described here, and data for these dose groups is depicted in FIG. 1*a*. A further dose group was 80 mg once daily, taken as an oral formulation as described here, and data for all dose groups including 80 mg once daily is depicted in FIG. 1*b*. This also shows further cycles of treatments for the 10, 20 and 40 mg once daily dose groups. The x axis shows the timepoint of sample collection with "Cx" meaning the x cycle of 28 days and "Dy" meaning the y day within the 28 day cycle. Accordingly C1D1 corresponds to day 1 of treatment, C1D8 corresponds to day 8 of treatment, etc and C2D1 corresponds to day 29 of treatment, C3D1 corresponds to day 57 of treatment, etc, each of a continuous treatment period.

Surprisingly it was observed that treatment of patients with Compound 1 did not result in any clinically significant treatment-related ALT elevation above the normal range. Even more surprising, treatment with Compound 1 resulted in a decrease of ALT levels in one patient that had elevated ALT levels before treatment with Compound 1. FIG. 1*b* shows Compound 1 resulted in a decrease of ALT levels in three patients that had elevated ALT levels at cycle 1 day 1 before treatment with Compound 1. In one other patient ALT levels increased during treatment with Compound 1, however this increase was related to a growing tumour lesion in the liver.

This is surprising as it has been reported that treatment of patients with idelalisib results in elevated ALT levels in 42.9% of patients and is considered a PI3Kδ target and class specific toxicity (see Table 57 in CHMP assessment report on Zydelig).

Example 3

Measurement of AST Levels in Blood Samples of Patients Treated with Compound 1

Figure 2A:
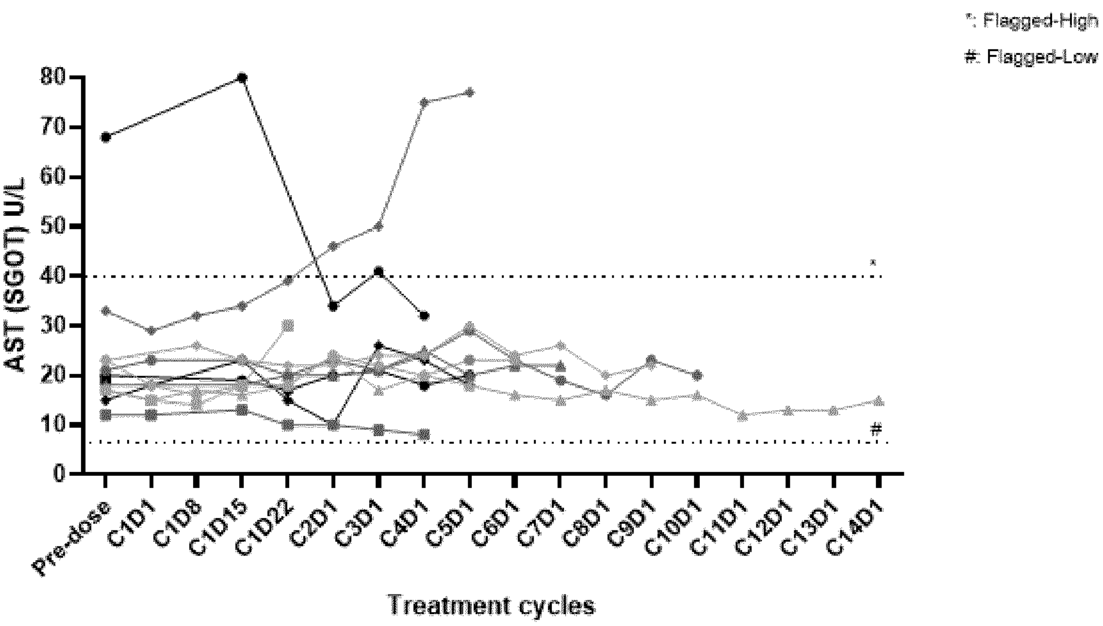
FIGS. 2*a* and 2*b* show measured AST levels in patients treated with Compound 1.
Figure 2B:
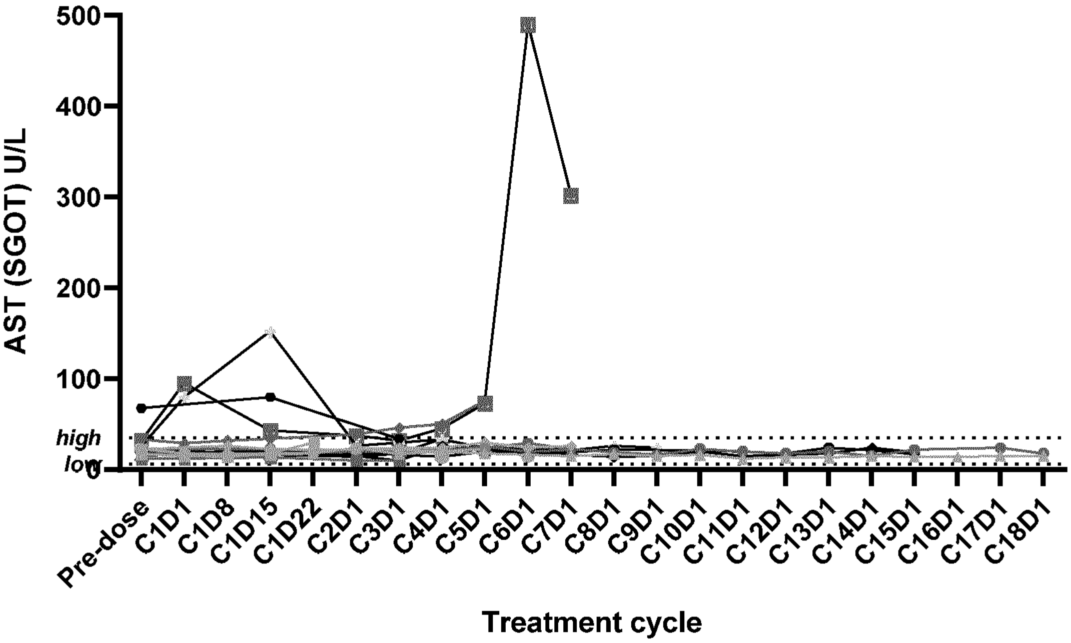

The hepatotoxicity of Compound 1 in patients was determined by measuring the levels AST in blood samples of patients treated with Compound 1. The initial dose groups were 10, 20 and 40 mg once daily, taken as an oral formulation as described here, and data for these dose groups is depicted in FIG. 2*a*. A further dose group was 80 mg once daily, taken as an oral formulation as described here, and data for all dose groups including 80 mg once daily is depicted in FIG. 2*b*. This also shows further cycles of treatments for the 10, 20 and 40 mg once daily dose groups.

Surprisingly it was observed that treatment of patients with Compound 1 did not result in any clinically significant treatment-related AST elevation above the normal range. Even more surprising, treatment with Compound 1 resulted in a decrease of AST levels in one patient that had elevated AST levels before treatment with compound 1. Even more surprising, treatment with Compound 1 resulted in a decrease of AST levels in three patients that had elevated AST levels at cycle 1 day 1 before treatment with compound 1. In one other patient AST levels increased during treatment with Compound 1, however this increase was related to a growing tumour lesion in the liver.

The finding that treatment with Compound 1 does not increase AST levels is surprising as it has been reported that treatment of patients with idelalisib results in elevated AST levels in 41.8% of patients and is considered a PI3Kδ target and class specific toxicity (see Table 57 in CHMP assessment report on Zydelig).

Example 4

Reported Treatment-Related Adverse Events (AEs) of Patients Treated with Compound 1

AEs related to treatment reported for patients treated with Compound 1 by the treating physician are mild and of grade 1 except for one occasion of uveitis grade 2. Surprisingly, it was observed that treatment of patients with Compound 1 did not result in the typical toxicities observed for other PI3Kδ inhibitors such as diarrhoea/colitis and (respiratory) infections. There was only one case of suspected diarrhoea but this case was mild (grade 1) and of short duration (2 days) and thus could also be related to an incidence of food poisoning. There were no cases of colitis or (respiratory) infections. This is very surprising as it has been reported that treatment of patients with idelalisib results in diarrhoea/colitis in 38.2% of patients and in infections in 59.3% of patients (see Table 49 in CHMP assessment report on Zydelig). Table 2 documents adverse events assessed by the investigator as related to treatment with Compound 1. No adverse effects were recorded in patients dosed at 80 mg QD.

TABLE 2

| System organ class Preferred term | 10 mg N = 4 | 20 mg N = 4 | 40 mg N = 4 | 80 mg N = 4 | Total N = 16 |
|---|---|---|---|---|---|
| Decreased appetite | 1 | 0 | 0 | 0 | 1 (6.3%) |
| Taste change | 1 | 0 | 0 | 0 | 1 (6.3%) |
| Dry face skin | 1 | 0 | 0 | 0 | 1 (6.3%) |
| Asthenia | 0 | 1 | 0 | 0 | 1 (6.3%) |
| Diarrhoea | 0 | 0 | 1 | 0 | 1 (6.3%) |
| Headache | 0 | 0 | 1 | 0 | 1 (6.3%) |
| Lethargy | 0 | 0 | 1 | 0 | 1 (6.3%) |
| Uveitis | 0 | 0 | 1 | 0 | 1 (6.3%) |

Example 5

Measurement of Neutrophils in Blood Samples of Patients Treated with Compound 1

Figure 3A:
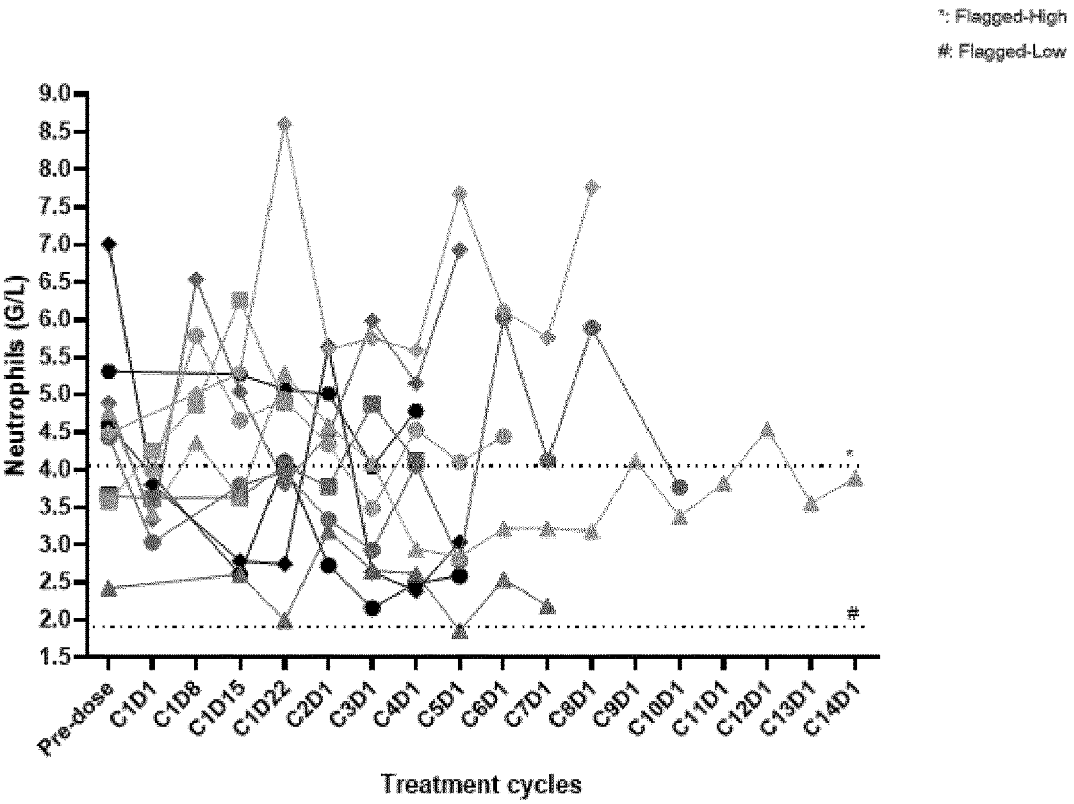
FIGS. 3*a* and 3*b* show measured neutrophils in patients treated with Compound 1.
Figure 3B:
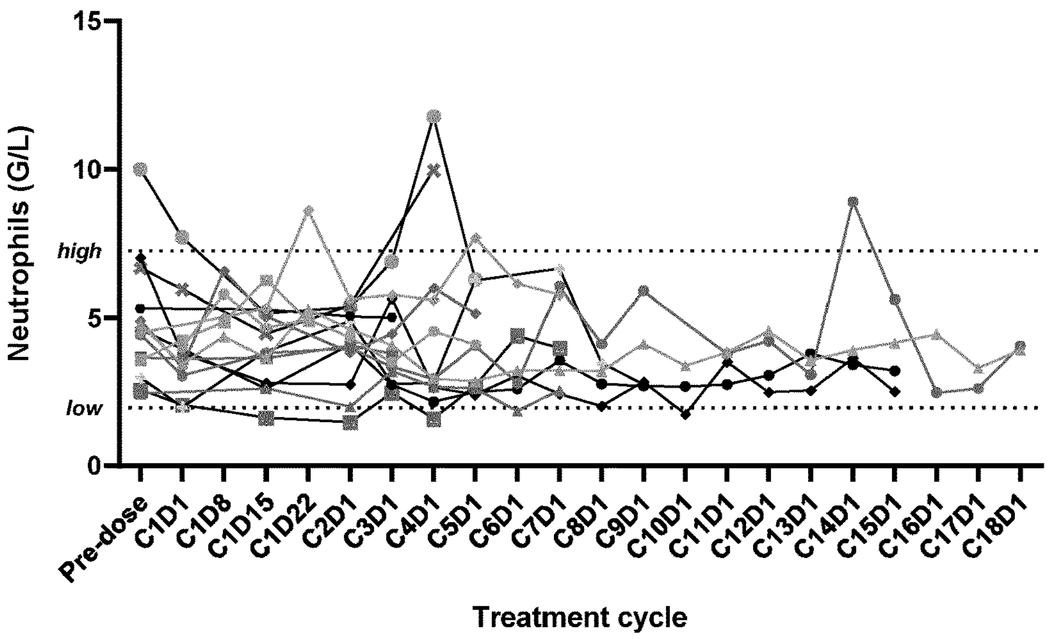

The heamatological toxicity of Compound 1 in patients was determined by measuring the neutrophil counts in blood samples of patients treated with Compound 1. The initial dose groups were 10, 20 and 40 mg once daily, taken as an oral formulation as described here, and data for these dose groups is depicted in FIG. 3*a*. A further dose group was 80 mg once daily, taken as an oral formulation as described here, and data for all dose groups including 80 mg once daily is depicted in FIG. 3*b*. This also shows further cycles of treatments for the 10, 20 and 40 mg once daily dose groups.

Surprisingly it was observed that treatment of patients with Compound 1 did not result in clinically significant treatment-related decrease in neutrophils below the normal range.

This is surprising as it has been reported that treatment of patients with idelalisib results in decreased neutrophil counts in 45.5% of patients and is considered a PI3Kδ target and class specific toxicity (Table 55 in CHMP assessment report on Zydelig).

Example 6

CD63 Marker Information

Figure 4A:
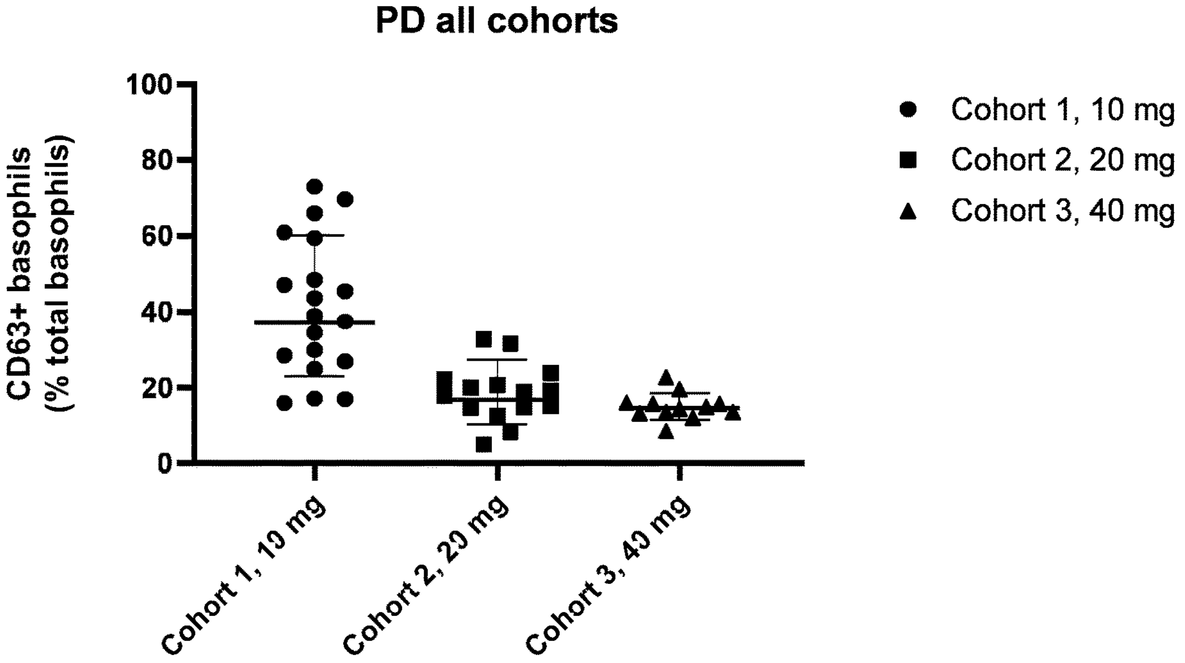
FIGS. 4*a* and 4*b* show measured CD63 positive basophils in patient treated with Compound 1 after ex vivo stimulation with anti-IgE.
Figure 4B:
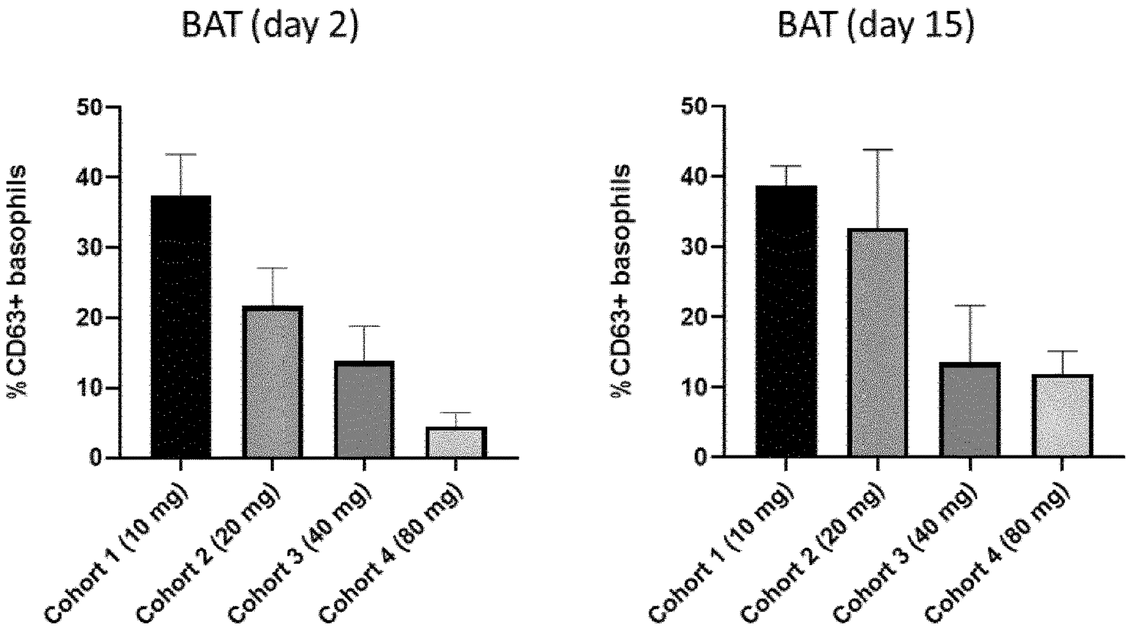

The pharmacodynamic (PD) activity of Compound 1 in patients was determined by measuring the percentage of CD63 positive basophils in blood samples of patients treated with Compound 1 after ex vivo stimulation with anti-IgE using the basophil activation test (BAT). See FIG. 4*a* and FIG. 4*b*.

Degranulation of basophils following crosslinking of FcεR1 receptor has been shown to be PI3Kδ-dependent (Ali 2008) and the activity of PI3Kδ inhibitors on basophil degranulation can be measured by the inhibition of ex vivo IgE-mediated CD63 expression (Lannutti 2011). Compound 1 shows a dose dependent reduction of CD63 positive basophils in blood samples of patients comparable to that reported for idelalisib (Horak 2016).

REFERENCES

A number of publications are cited above in order to more fully describe and disclose the invention and the state of the art to which the invention pertains. Full citations for these references are provided below. The entirety of each of these references is incorporated herein.

WO2011058149
WO201412190
CHMP assessment report on Zydelig (2014)
Ali, K. et al. (2008). Isoform-Specific Functions of Phosphoinositide 3-Kinases: p110δ but Not p110γ Promotes Optimal Allergic Responses In Vivo. J Immunol 180, 2538-2544.
Brock, C. et al. (2003). Roles of Gβγ in membrane recruitment and activation of p110γ/p101 phosphoinositide 3-kinase γ. J Cell Biology 160, 89-99.
Buchanan, C. M. Et al. (2019). For Better or Worse: The Potential for Dose Limiting the On-Target Toxicity of PI 3-Kinase Inhibitors. Biomol 9, 402.
Curigliano and Shah (2019). Safety and Tolerability of Phosphatidylinositol-3-Kinase (PI3K) Inhibitors in Oncology. Drug Saf. 42 (2), 247-262.
Esposito, A. Et al. (2019). Safety, Tolerability, and Management of Toxic Effects of Phosphatidylinositol 3-Kinase Inhibitor Treatment in Patients With Cancer. Jama Oncol 5, 1347-1354.
Haselmayer, P. et al., Frontiers in Immunology (2014), Vol. 5, Art. 233, p. 1-15; see p. 2, col. 2, section "Chemical Synthesis", par. 1

Horak, F. et al. (2016). Randomized phase 1 study of the phosphatidylinositol 3-kinase δ inhibitor idelalisib in patients with allergic rhinitis. J Allergy Clin Immun 137, 1733-1741.

Jimenez, C. et al. (2002). The p85 regulatory subunit controls sequential activation of phosphoinositide 3-kinase by Tyr kinases and Ras. J Biol Chem 277, 41556-62.

Johnson, Z. et al., AACR 2020, poster 666

Lannutti, B. J. et al. (2011). CAL-101, a p110δ selective phosphatidylinositol-3-kinase inhibitor for the treatment of B-cell malignancies, inhibits PI3K signaling and cellular viability. Blood 117, 591-594

Phillips, T. J. et al. (2020). Can Next-Generation PI3K Inhibitors Unlock the Full Potential of the Class in Patients With B-Cell Lymphoma? Clin Lymphoma Myeloma Leukemia 21, 8-20.e3.

Vanhaesebroeck, B. et al. (2005). Signalling by PI3K isoforms: insights from gene-targeted mice. Trends Biochem Sci 30, 194-204.

For standard molecular biology techniques, see Sambrook, J., Russel, D. W. Molecular Cloning, A Laboratory Manual. 3 ed. 2001, Cold Spring Harbor, New York: Cold Spring Harbor Laboratory Press.

The invention claimed is:

1. A method of treating uveal melanoma or mesothelioma in a subject in need thereof, comprising administering to the subject a compound of Formula I wherein the compound of Formula I is Formula I

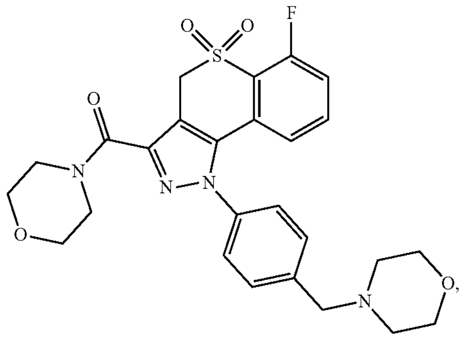

or a pharmaceutically acceptable salt thereof.

2. The method of claim 1, wherein the compound of Formula I is administered at a dose of about 36 mg per day.

3. The method of claim 1, wherein the compound of Formula I is administered at a dose of about 72 mg per day.

4. The method of claim 1, wherein the compound is a hemifumarate salt according to Formula Ia Formula Ia

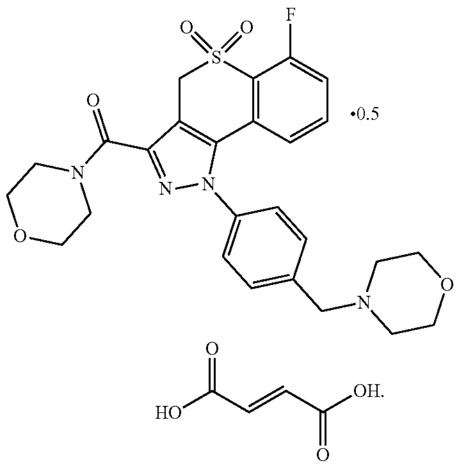

5. The method of claim 4, wherein the compound is administered at a dose of about 40 mg per day.

6. The method of claim 4, wherein the compound is administered at a dose of about 80 mg per day.

7. The method of claim 4, wherein the administration is once daily.

8. The method of claim 4, wherein the administration comprises one solid dosage units comprising 40 mg or 80 mg of a salt of Formula Ia.

9. The method of claim 4, wherein the administration comprises two solid dosage units, each dosage unit comprising 20 mg or 40 mg of a salt of Formula Ia.

10. The method of claim 4, wherein the administration comprises four solid dosage units, each dosage unit comprising 20 mg of a salt of Formula Ia.

11. The method of claim 1, wherein the method comprises treating uveal melanoma.

12. The method of claim 1, wherein the method comprises treating mesothelioma.

13. The method of claim 4, wherein the method comprises treating uveal melanoma.

14. The method of claim 4, wherein the method comprises treating mesothelioma.

* * * * *